United States Patent [19]

Obitsu

[11] Patent Number: 5,797,857
[45] Date of Patent: Aug. 25, 1998

[54] GUIDE WIRE

[75] Inventor: Hideshi Obitsu, Fujinomiyasshi, Japan

[73] Assignee: Terumo Kabushiki Kaisha, Tokyo, Japan

[21] Appl. No.: 683,133

[22] Filed: Jul. 18, 1996

Related U.S. Application Data

[63] Continuation of Ser. No. 363,350, Dec. 23, 1994, abandoned.

[30] Foreign Application Priority Data

Dec. 24, 1993 [JP] Japan ................. 5-068751 U

[51] Int. Cl.$^6$ .................................................. A61B 5/00
[52] U.S. Cl. ............................................................ 600/585
[58] Field of Search ........................... 128/657, 658, 128/772; 604/95, 164, 280–283; 600/585

[56] References Cited

U.S. PATENT DOCUMENTS

| | | | |
|---|---|---|---|
| 4,534,363 | 8/1985 | Gold | 128/772 |
| 4,545,390 | 10/1985 | Leary | 128/344 |
| 4,721,117 | 1/1988 | Mar et al. | 128/772 |
| 4,724,846 | 2/1988 | Evans | 128/772 |
| 4,811,743 | 3/1989 | Stevens | 128/772 |
| 4,884,579 | 12/1989 | Engelson | 128/772 |
| 5,111,829 | 5/1992 | Alvarez de Toledo | 128/772 |
| 5,129,890 | 7/1992 | Bates et al. | 604/281 |
| 5,174,302 | 12/1992 | Palmer | 128/772 |
| 5,238,004 | 8/1993 | Sahatjian et al. | 128/772 |
| 5,267,575 | 12/1993 | Viera et al. | 128/772 |
| 5,333,620 | 8/1994 | Moutafis et al. | 128/772 |
| 5,363,847 | 11/1994 | Viera | 128/772 |
| 5,452,726 | 9/1995 | Burmeister et al. | 128/772 |

FOREIGN PATENT DOCUMENTS

| | | | |
|---|---|---|---|
| 1324553 | 11/1993 | Canada. | |
| 0 405 823 | 1/1991 | European Pat. Off.. | |
| 4-009162 | 1/1992 | Japan. | |
| 8501444 | 4/1985 | WIPO | 128/772 |
| WO89/10088 | 11/1989 | WIPO. | |

*Primary Examiner*—Max Hindenburg
*Attorney, Agent, or Firm*—Burns, Doane, Swecker & Mathis, LLP

[57] ABSTRACT

A guide wire comprising a super-elastic core member which consists of a proximal section, a distal section smaller in diameter than the proximal section and a intermediate section between the proximal section and the distal section, an X-ray opaque metal coil attached to the distal section of the core member in tight contact with the distal section, a synthetic resin envelope which covers the core member and the X-ray opaque metal coil to form a substantially smooth outside surface, and a hydrophilic lubricative layer which covers the outside surface of the synthetic resin envelope. The distal section of this guide wire can be reshaped repeatedly. The X-ray visibility of the distal section is improved.

31 Claims, 7 Drawing Sheets

FIG. 5
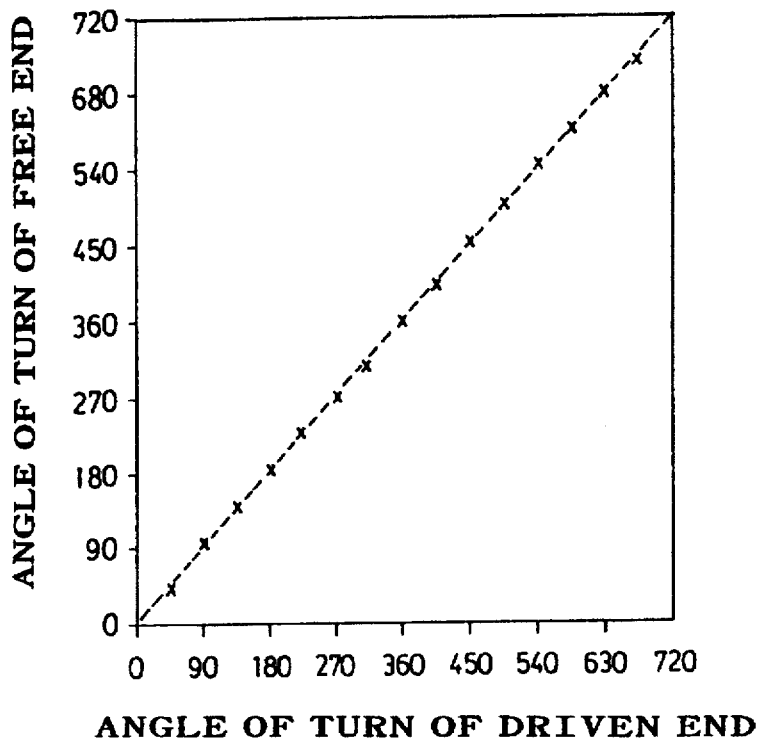
(a)
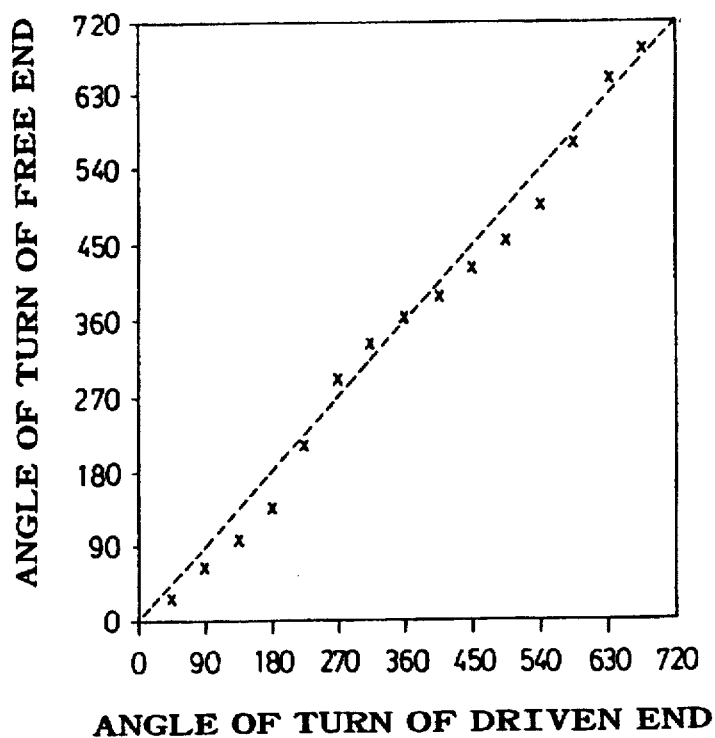
(b)

FIG. 6
(a)
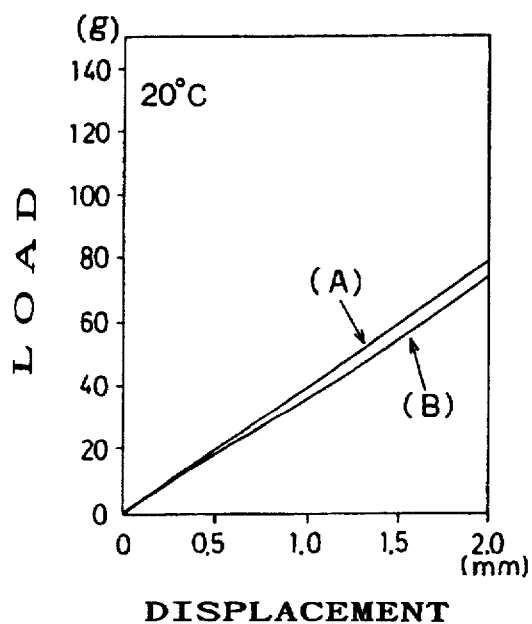
(b)
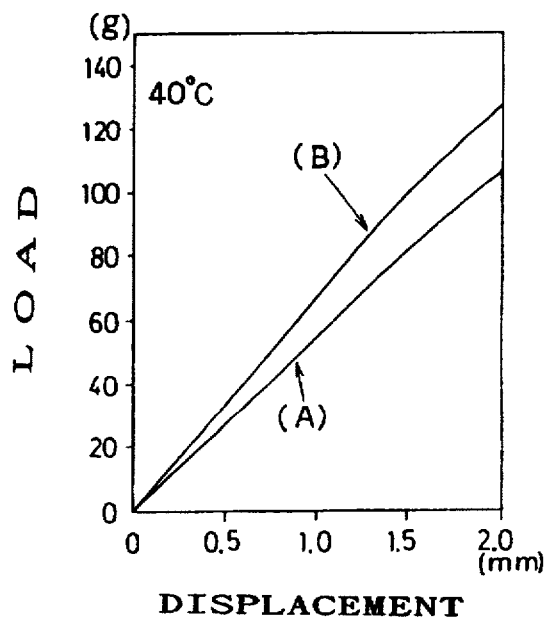
FIG. 7
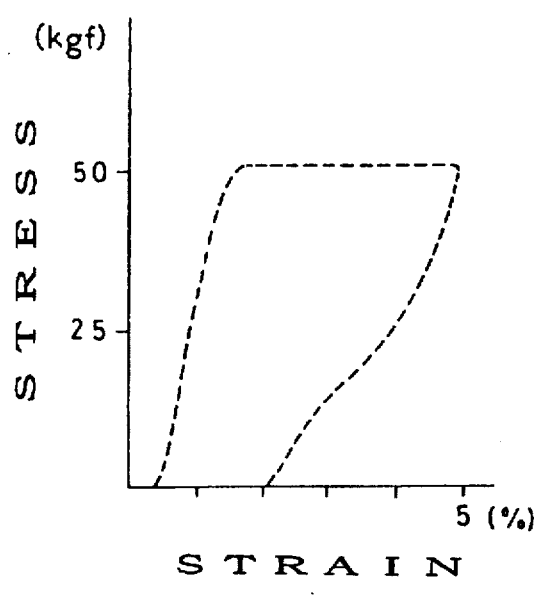

GUIDE WIRE

This application is a continuation of application Ser. No. 08/363,350, filed Dec. 23, 1994 now abandoned.

BACKGROUND OF THE INVENTION

This invention relates to a guide wire used to introduce a catheter to a desired part of a human body for treatment or examination purpose.

Introduction of a catheter into blood vessels has been practiced for examination or treatment of heart diseases. To introduce a catheter to the part aimed at in the body, a guide wire is passed through the catheter and advanced ahead of the catheter. After the guide wire reaches the part, the catheter is advanced along the guide wire to the part.

Especially in percutaneous transluminal coronary angioplasty (PTCA), the distal (lead) end of the guide wire is advanced to a stenosed part aimed at, selecting branches of the coronary artery under radiography or angiography, the distal end of the guide wire is passed through the stenosed part. Then, a dilatation catheter provided with a balloon near the distal end is advanced along the guide wire. The balloon is positioned at the stenosed part and inflated to widen the stenosed part. By thus restoring the blood flow, the hemostasis which is causing the angina pectoris is treated.

To advance the guide wire into the desired branch at the furcation in the coronary artery, the distal end of the guide wire must be formed into an appropriate shape matching the shape of the furcation by the hands (reshaping). Conventional angle type guide wires and guide wires with a J-shaped lead end are difficult to insert especially when they must be inserted into a coronary artery at the peripheral side. In such cases, the distal end of the guide wire is reshaped into a desired shape and used. When the shape of the distal end does not match the shape of the branch after the guide wire is inserted, the guide wire is pulled out to reshape the distal end, then inserted again.

Further, the force or the movement applied to the proximal side must be transmitted to the distal end in order to aim the distal end of the guide wire in the desired direction.

A contrast medium is injected into blood vessels intermittently to identify the desired coronary artery with irradiation of X rays. Manipulation of the distal end of the guide wire is also performed keeping track of the position of the distal end with irradiation of X rays. Therefore, there is desired for the distal end of the wire than that of the contrast medium used for angiography.

To insert from the femoral artery and advance into the coronary artery via the aorta, the aortic arch and the entrance of the coronary artery, the guide wire needs an adequate flexibility to bend along the blood vessels and a high capability of transmitting the pushing force applied to the proximal side to the distal end (pushability).

To position the balloon of a dilation catheter in a stenosed or obstructed part and widen the passage, it is important to be able to pass the distal end of the guide wire through stenosed or obstructed parts. When passing the distal end of the guide wire through a stenosed or obstructed part, the proximal portion of the guide wire is pushed in while it is slowly rotated. The distal end of the guide wire must rotate smoothly in synchronism with the rotation of the proximal side. If an intermittent rotation (so called "bouncing") occurs at the distal end when the proximal side is rotated at a constant speed, such a guide wire is difficult to pass through stenosed or obstructed parts.

There are guide wires disclosed in U.S. Pat. No. 4,545,390 and Canadian Patent 1,324,553.

The guide wire shown in U.S. Pat. No. 4,545,390 has the distal section of the main wire member tapered toward the distal end and a spring member attached on the tapered section only. The guide wire shown in Canadian Patent 1,324,553 has the distal section of the inner core member tapered and a high contrast X-ray shadow producing spring member attached on the distal end.

The guide wire of U.S. Pat. No. 4,545,390 is difficult to use reshaping repeatedly because of its getting into a habit of bending from previous reshaping. Especially, it is difficult that the distal end of the guide wire is formed into a low angle shape (ex. 60 degree with a center axis of the guide wire) by second reshaping after the distal end of the guide wire was formed into a high angle shape (ex. 90 degree with the center axis of the wire) by first reshaping. Therefore, a new guide wire must be used when a differently shaped distal section is required. Moreover, since the spring member at the distal section is exposed, the unevenness of the surface causes a resistance when the guide wire is inserted through stenosed parts. Especially when the stenosed part is narrower than the outer diameter of the distal section of the guide wire, even a small unevenness of the surface can cause a considerable resistance against insertion. Because of this resistance caused by the spring member, the insertion through stenosed parts of the guide wire, especially the one with a very flexible, easily bending distal section, is difficult.

The guide wire of Canadian Patent 1,324,553 has the high contrast X-ray shadow producing spring member, which practically cannot be reshaped.

The present invention was made to solve the problems with conventional guide wires describe above.

The object of the present invention is to provide a guide wire which can be reshaped, especially repeatedly and accurately into any desired shape or form, has a high X-ray visibility, and can be easily passed through stenosed parts.

Another object of the present invention is to provide a guide wire which can transmit a torque and pushing force applied to the proximal side to the distal end with high fidelity and hence has a high manipulatability.

SUMMARY OF THE INVENTION

The guide wire of the present invention comprises a super-elastic core member having a proximal section, a distal section smaller in diameter than the proximal section and an intermediate section between the proximal section and the distal section, an X-ray opaque metal coil attached to the distal section of the core member in tight contact with the distal section, a synthetic resin envelope which covers the core member and the X-ray opaque metal coil to form a substantially smooth outside surface, and a hydrophilic lubricative layer which covers the outside surface of the synthetic resin envelope.

BRIEF DESCRIPTION OF THE DRAWINGS

FIGS. 5(a) and 5(b) are line graphs which show the torque-transmitting capabilities of the super-elastic core members.

FIGS. 6(a) and 6(b) are line graphs which show the rigidities of the super-elastic core members.

FIG. 7 illustrates a stress-strain curve of the core member used for a distal section of the third embodiment of the guide wire of the present invention.

FIG. 10 is a cross-sectional view of a portion of the distal end of the core member illustrating the slightly tapering nature of the outer diameter.

DETAILED DESCRIPTION OF THE PREFERRED EMBODIMENTS

Figure 1:
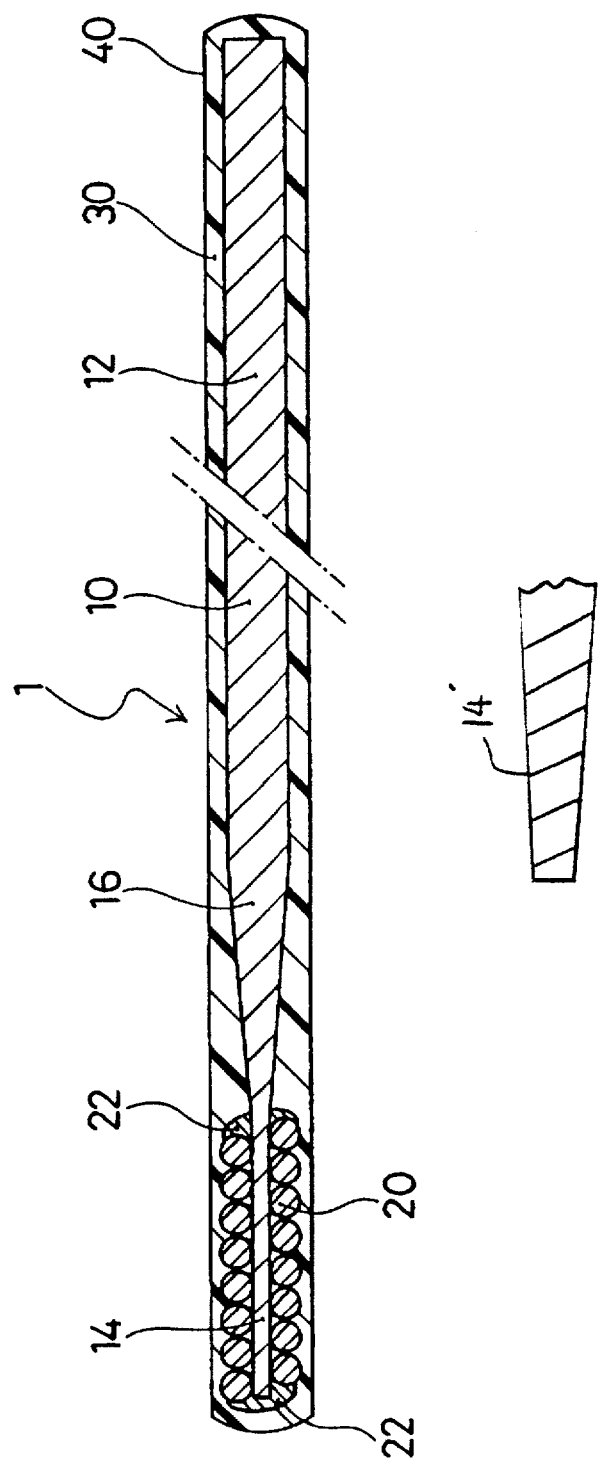
FIG. 1 is a sectional view of a first embodiment of a guide wire of the present invention.

The guide wire of the present invention is described below using the embodiments shown in the drawings.

As shown in FIG. 1, the guide wire 1 of the present invention comprises a super-elastic core member 10 consisting of a proximal section 12, a distal section 14 smaller in diameter than the proximal section 12, and a intermediate section (in other words, middle section or transitional section) 16 between the proximal section 12 and the distal section 14 which becomes gradually smaller in diameter from the proximal section to the distal section, an X-ray opaque (shadow producing) metal coil 20 attached closely to the distal section 14 of the core member 10, a synthetic resin envelope 30 which covers the outside surface of the core member 14 and the X-ray opaque metal coil 20 to form a substantially smooth outside surface, and a hydrophilic lubricative layer 40 which covers the outside surface of the synthetic resin envelope 30.

The super-elastic core member 10 has the proximal section 12, the intermediate section 16, and the distal section 14, from the proximal side toward the distal side.

The distal section 14 of the super-elastic core member preferably has an approximately uniform outer diameter or is slightly tapered toward the distal end. FIG. 1 shows the distal section 14 of the core member being provided with an approximately uniform outer diameter while FIG. 10 shows a different form of the distal section 14' of the core member in which the outer diameter is slightly tapered toward the distal end. By thus forming the distal section 14, it has an approximately uniform flexibility in the direction of the axis. The distal section 14 has the highest flexibility compared to the intermediate and proximal sections.

The intermediate section 16 is the portion which becomes gradually smaller in diameter toward the distal section 14. This portion, which is also referred to as the "tapered portion", may become smaller in diameter in a uniform taper or in different tapers, for example, in steps, unless an abrupt change in the physical property (flexibility or rigidity) is not caused between the distal section 14 and the proximal section 16. By forming such a intermediate section 16 in the super-elastic core member, a high flexibility is given to the distal section of the guide wire without the concentration of stress which causes kinking.

The proximal section 12 is the portion which extends from the intermediate section 16 to the proximal end. The proximal section 12 has a greater diameter than the distal section 14 so that it can transmit the torque and pushing force applied to the proximal end portion of the guide wire to the distal section with high fidelity.

The distal section and the intermediate section may be a continued portion which becomes gradually smaller in diameter at about the same taper (rate of diminution) from the outer diameter of the proximal section, which is uniform throughout the length of the proximal section. The X-ray opaque coil 20 may be divided into two or more portions which are attached on the distal section at appropriate spaces.

In a preferred embodiment, the intermediate section 16 of the super-elastic core member is more flexible than the proximal section 12, and the distal section 14 is more flexible than the intermediate section 16. To provide the super-elastic core member with this property, the proximal section of the super-elastic core member is formed in a larger outer diameter, the distal section in a smaller outer diameter, and the intermediate section is tapered so as to connect the proximal section and the distal section with a gradual change in the physical property.

Also for this embodiment, the distal section is preferably of a uniform diameter or slightly tapered.

Figure 8:
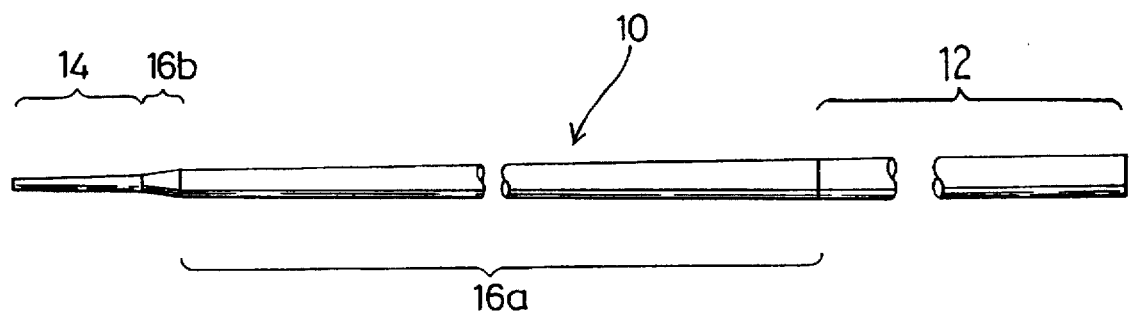
FIG. 8 is a lateral view of the intermediate and distal sections of a super-elastic core member used for a guide wire of the present invention.

The intermediate section has preferably two portions with different tapers: first intermediate section 16a with a smaller taper and second intermediate section 16b with a larger taper, as shown in FIG. 8. By this form of the intermediate section, the occurrence of an abrupt change in the physical property of the super-elastic core member around the rear end of the coil 20 can be prevented. That is, the composite member constituted of the core member 10 and the coil 20 wound changes to the core member alone at the rear end of the coil 20, and therefore a point of abrupt change in the physical property can occur. However, the second intermediate section 16b is formed at the distal side part of the intermediate section 16, and the second intermediate section 16b has a taper greater than that of the first intermediate section 16a at the proximal side part as described above, formation of a visible point of abrupt change in the physical property can be prevented. Thereby bending of the core member becomes smoother. The length of the second intermediate section is preferably about 0.03 to 0.2 times the length of the first intermediate section. The taper of the second intermediate section is preferably about 3 to 40 times the taper of the first intermediate section.

The dimensions of the super-elastic core member vary depending on the use of the guide wire. For the super-elastic core member with the distal section, intermediate section, and proximal section used for a PTCA guide wire, for example, the outer diameter of the distal section is within the range of 0.06 to 0–12 mm, preferably 0.06 to 0.10 mm, and the length is within the range of 10 to 50 mm; the length of the intermediate section is within the range of 50 to 600 mm; and the outer diameter of the proximal section is within the range of 0.26 to 0.50 mm, and the length is within the range of 1000 to 3000 mm.

The core member is made of a super-elastic material so that it has an appropriate flexibility needed for bending along blood vessels along with an appropriate rigidity for transmitting the torque and pushing force applied to the proximal end portion to the distal end. The super-elastic material includes Ni—Ti alloy, Cu—Zn—X alloy (X=Be, Si, Sn, Al or Ga), and Ni—Al alloy. Ni—Ti alloy is preferable. A third element such as Co or Fe may be added to Ni—Ti alloy.

The distal section, intermediate section, and proximal section of the super-elastic core member may have the same physical property, or the distal section or the proximal section alone may have a different physical property.

The X-ray opaque coil is attached to the distal section of the core member in tight contact with the surface of the distal end. Materials which are comparatively opaque to X rays and provides a high visibility by radiography include gold, platinum, silver, bismuth, tungsten, or alloys of two or more of them (platinum-tungsten, for example) or alloys of one of them and other metals (gold-iridium or platinum-iridium, for example). The X-ray opaque coil may be plated with another material.

Although there is no particular limitation on the outer diameter of the X-ray opaque coil unless it has a satisfactory reshapability, manipulatability, and X-ray visibility, the X-ray visibility increases with the outer diameter of the coil. On the other hand, the transmission of torque is made easier by the outer diameter of the metal coil equal to or smaller than that of the core member. For a core member with the distal section, intermediate section and proximal section as of this embodiment, the outer diameter of the X-ray opaque coil is preferably equal to or smaller than the largest outer diameter of the core member or the outer diameter of the proximal section. By use of such an X-ray opaque coil, the outer diameter of the distal section of the core member with the coil attached does not exceed the outer diameter of the proximal section of the core member.

The length of the metal coil in the direction of the axis should allow reshaping and is within the range of 10 to 40 mm, preferably 15 to 40 mm, and especially preferably 20 to 30 mm.

The material for the coil is one of the above mentioned metals and has a Vickers Hardness preferably within the range of 90 to 300 and especially preferably within the range of 120 to 250, from the point of ease of deforming and the stability of the shape into which the metal coil is reshaped. To put it concretely, an alloy of platinum (90% to 95%) and iridium (10% to 5%) is preferable.

The diameter of the wire for forming the coil is within the range of about 0.03 to 0.15 mm or about 112 to 2 times the outer diameter of the distal section of the core member.

Figure 9:
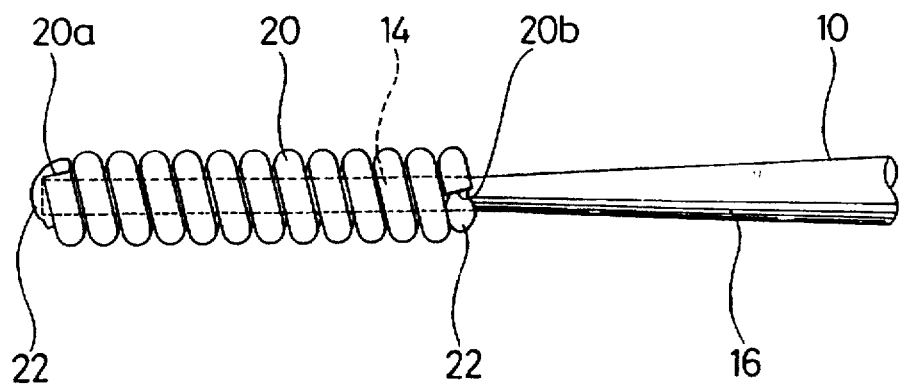
FIG. 9 is a lateral view of the distal section of a guide wire of the present invention with a synthetic resin envelope stripped.

The wire is wound sparsely in order to make a deformation of the coil easier. Thereby, the coil 20 has narrow spaces between turns as shown in FIG. 9, in other words, the coil 20 has a narrow spiral space. The coil is hard to deform if the adjacent turns are in close contact with each other, but a sparsely wound coil can deform easily. However, the X-ray visibility of the coil decreases with the distance between the turns. Therefore, the distance between the turns is preferably within the range of about 5/100 to ½ time diameter of the wire or about 5/100 to ½ time outer diameter of the distal section of the core member.

The tight fitting of the X-ray opaque coil on the core member is accomplished by winding the X-ray opaque metal wire or by inserting the distal section of the core member through the X-ray opaque coil wound in advance in an inner diameter nearly equal to the outer diameter of the distal section of the core member. Both ends of the coil is secured to the core member with an adhesive or by soldering or welding. Further, the coil can be more reliably secured by forming at the distal end of the core member a larger-diameter portion such as a bulb which has an outer diameter a little greater than the inner diameter of the metal coil and securing the front end of the metal coil to the larger-diameter portion. The bulb larger-diameter portion can be formed by melting the core member.

It is preferable to secure at least the front edge of the metal coil to the core member with an adhesive or by soldering. With the front end secured, the coil cannot damage the synthetic resin envelope when it deforms. Further, by securing both ends of the coil, change in the distance between the turns and the length of the coils are suppressed and reshaping of the coil is made easier.

Securing with an adhesive is preferable, because it does not heat the core member partly as soldering does and therefore there is no need to worry about causing a change in the physical property of the core member. For the adhesive, any adhesive which can bond the super-elastic metal and the X-ray opaque metal coil may be used. For example, an epoxy adhesive or an urethane adhesive can be used, and an epoxy adhesive is especially preferable.

It is preferable that the front end 20a and rear end 20b of the wire of the coil 20 are cut at an approximately right angle with the center axis of the wire. The securing force of the adhesive 22 is stronger for the wire ends cut at a right angle with the wire axis than for those cut obliquely, and hence movement of the coil ends caused by the force exerted when the coil is deformed can be prevented.

By attaching the X-ray opaque metal coil to the super-elastic core member in tight contact with the outer surface of the core member, reshaping using a plastic deformation of the metal coil is made possible. Since the core member does not undergo a plastic deformation because of its super elasticity if the metal coil is plastic-deformed, repeated reshaping of the distal section of the guide wire into various shapes is possible.

The core member 10 and the X-ray opaque metal coil 20 are covered with a synthetic resin envelope or cover 30.

Specifically, the synthetic resin envelope 30 envelopes the core member 10 and the X-ray opaque metal coil 20 and forms a substantially smooth outside surface. The guide wire with the synthetic resin envelope formed has preferably an approximately uniform outer diameter from the distal end to the proximal end. The distal section may be formed in a smaller outer diameter than the other portion of the guide wire for the purpose of increasing the flexibility of the distal section or making it easier to pass the guide wire through stenosed parts in blood vessels.

It is also possible to cover only the distal section containing the metal coil and its vicinity, wherein the front end of the cover is positioned at the distal side from the front end of the metal coil and the rear end of the cover is positioned at the proximal side from the rear end of the metal coil. In this structure, it is preferable to apply silicone to the exposed surface of the core member.

The envelope is formed of a synthetic resin because of a synthetic resin being easy to form and the surface of the synthetic resin envelope being easy to treat as described below. The synthetic resin envelope is flexible enough not to prevent bending of the core member, and the outer surface is substantially smooth.

Powder of an X-ray opaque material may be mixed into the synthetic resin for forming the envelope. For the powder X-ray opaque material, tungsten, bismuth and barium, for example, can be used. By covering a part or the whole of the core member with the synthetic resin containing an X-ray opaque material, the X-ray visibility of that part or the whole of the guide wire increases. Especially, by covering the distal section of the core member with the synthetic resin containing an X-ray opaque material, the X-ray visibility of the distal section of the guide wire further increases.

The flexibility of the synthetic resin envelope may be changed according to the flexibility of the core member. Specifically, different synthetic resins are used for the distal section, the intermediate section, and the proximal section of the core member. For example, a most flexible (and soft) material is used for the distal section which is inserted into blood vessels and pressed against the wall of blood vessels; a most rigid material is used for the proximal section in order to reinforce the torsional rigidity and the bending rigidity of the proximal section; and a material with an intermediate rigidity is used for the intermediate section. For the intermediate section, two materials with different rigidities may also be used gradually increasing the proportion of the material with a lower rigidity toward the distal end. This method is preferable because an abrupt change in the torsional rigidity can be prevented.

The synthetic resin envelope may be formed of two or more layers. For example, the proximal section of the core member is covered with a resin having a comparatively high rigidity such as polyimide resin in order to reinforce the rigidity. The inner layer is made of this resin cover. Over this inner layer, the outer layer is formed of a resin with a plenty of reactive groups which bind a hydrophilic lubricative substance. A lubricative layer of a hydrophilic substance is fixed to the outer layer.

It is also possible to form the inner layer using an adhesive resin such as ionomer in order to increase the adhesive strength between the super-elastic core member and the resin layer and thereby improve the torque transmission capability of the guide wire. Over this inner layer, the outer layer is formed of a resin with a plenty of reactive groups which bind a hydrophilic lubricative substance. A lubricative layer of a hydrophilic substance is fixed to the outer layer. A layer of a resin with a low coefficient of friction such as fluororesin may be formed on the outside surface of the cover.

For the material for the synthetic resin envelope, polyurethane, polyethylene, polyvinyl chloride, polyester, polypropylene, polyamide, polystyrene, fluororesin, silicone, their elastomer (polyester elastomer, for example), or a composite material of two or more of them can be used.

The hydrophilic lubricative layer which covers the outside surface of the synthetic resin envelope exhibits a hydrophilic property when it gets wet, and their lubricity increases. By forming this hydrophilic lubricative layer, the frictional resistance between the inside surface of a catheter and blood vessels can be reduced and a high lubricity is imparted to the guide wire.

The hydrophilic lubricative layer may be fixed to the synthetic resin envelope by chemical combination (ionic bond or covalent bond) or by a physical force.

The hydrophilic lubricative layer is formed of a hydrophilic lubricative substance coated on the outside surface of the envelop. A hydrophilic lubricative substance which exhibits a lubricity when it gets wet is preferable, and a preferable hydrophilic lubricative substance is a water-soluble high-molecular substance. The hydrophilic lubricative substance may be fixed to the outside surface of the envelop.

For the hydrophilic lubricative substance, high-molecular substances containing hydrophilic groups such as —OH, —CONH$_2$, —COOH, —NH$_2$, —COO— and —SO$^3$— are preferable. Those preferable substances include methyl vinyl ether-maleic anhydride copolymer, methyl vinyl ether-maleic anhydride soda, methyl vinyl ether-maleic anhydride ammonium salt, maleic anhydride-ethyl ester copolymer as maleic anhydride derivative, polyethylene oxide as polyalkyne oxide, polyethylene glycol as polyalkylene glycol, and polyacrylic acid soda as acrylic acid derivative.

The hydrophilic lubricative substance is desirably a copolymer of hydrophilic compound and hydrophobic compound, and more desirably a block copolymer of hydrophilic compound and hydrophobic copolymer. Such block copolymers of hydrophilic compound and hydrophobic compound include poly(glycidyl methacrylate) (PGMA)-dimethyl acrylamide (DMAA), methacrylchloride-DMAA, methacryloyloxyethylisocyanate-DMAA, poly(glycidyl acrylate)-maleic anhydride.

The hydrophobic compound of such a copolymer combines with the synthetic resin envelope as the foundation, and the hydrophilic compound binds water and swells to reduce the coefficient of friction.

The outside surface of the synthetic resin envelope may also be coated with an anticoagulant such as heparin and urokinase or an anti-thrombogenic material such as silicone rubber, block copolymer of urethane and silicone, or hydroxyethylmethacrylate-styrene copolymer.

Concrete embodiments of the guide wire according to the present invention are described below.

As shown in FIG. 1, the guide wire 1 of the first embodiment of the present invention comprises a super-elastic core member 10 having a proximal section 12, a distal section 14 smaller in diameter than the proximal section 12 and a intermediate section 16 between the proximal section 12 and the distal section 14, an X-ray opaque metal coil 20 attached to the distal section 14 of the core member 10 in tight contact with the distal section, a synthetic resin envelope 30 which covers the outside surface of the core member 10 and the X-ray opaque metal coil 20 to form a substantially smooth outside surface, and a hydrophilic lubricative layer 40 over the outside surface of the synthetic resin envelope 30.

The guide wire 1 of this embodiment has an overall length of 180 cm and an outer diameter of about 0.35 mm. The overall length of the guide wire 1 may be within the range of 80 to 500 cm. The outer diameter of the guide wire 1 is determined appropriately for the intended application, and the preferable outer diameter of the guide wire 1 for PTCA is equal to or smaller than 0.5 mm.

The super-elastic core member 10 consists of the distal section 14, the intermediate section 16, and the proximal section 12.

The distal section 14 has an approximately uniform outer diameter and an approximately uniform flexibility. This portion is most flexible compared to the intermediate section 16 and the proximal section 12. The outer diameter of the distal section 14 is about 0.1 mm, and the length is about 20 mm.

The intermediate section 16 becomes gradually smaller in diameter toward the distal section 14. In this embodiment, the intermediate section 16 becomes gradually thinner at a uniform taper, and can be referred to as the "tapered portion". The length of this intermediate section 16 is 300 mm. By intermediate section 16, the flexibility (bendability) of the guide wire can be continuously increased toward the distal end without an abrupt change which can cause kinking.

The proximal section 12 extends from the intermediate section 16 to the proximal end of the guide wire 1. This proximal section has a substantially uniform outer diameter of about 0.3 mm and a length of about 1500 mm. The proximal section 12 is thicker than the distal section 14 so that it can transmit the torque and pushing force applied to the proximal portion to the distal section 14 with high fidelity.

The distal section 14, the intermediate section 16 and the proximal section 12 of the core member 10 constitutes a single solid member made of the same material. By forming them in a single solid member, occurrence of breaking and kinking can be prevented. This core member 10 is made of a super elastic metal, Ni—Ti alloy. The core member 10 made of a super elastic metal does not get into a habit of bending and has a high torque-transmitting capability even when it is in winding blood vessels.

Figure 4:
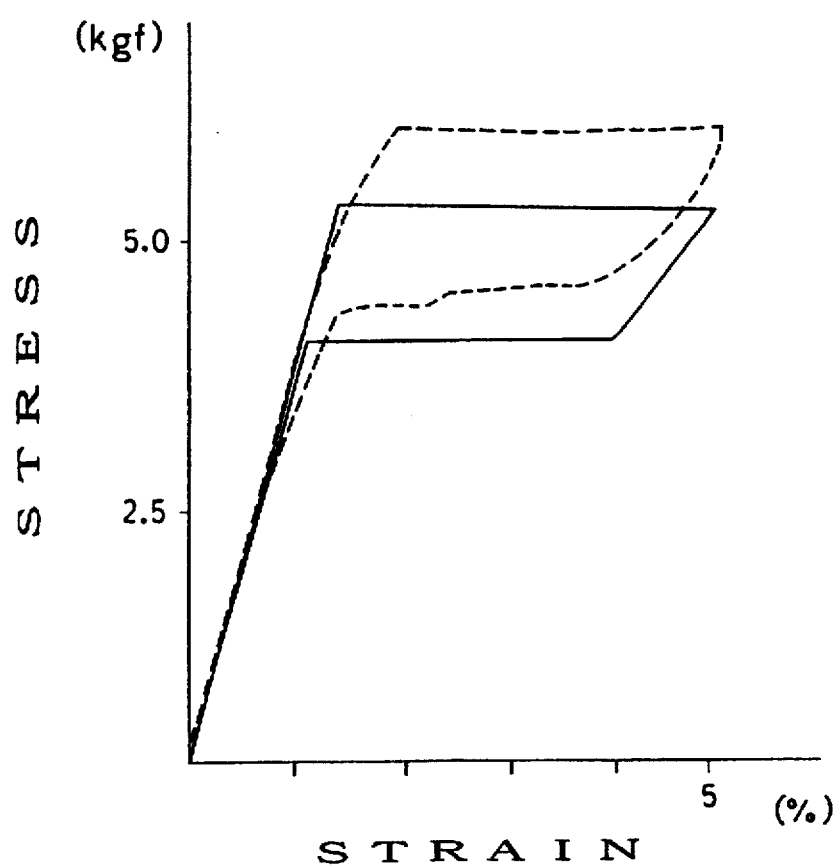
FIG. 4 illustrates stress-strain curves of super-elastic core members obtained by tension tests.

FIG. 4 illustrates stress-strain curves of super-elastic core members obtained by tension tests. These outer diameters of the core members were 0.343 mm. These core members are made of Ni—Ti alloy. These core members were subjected to 5% tension test at 40° C. The solid line in the graph shows the stress-strain characteristic of the core member 10 of the invention. The broken line shows the stress-strain characteristic of a super-elastic wire made of the same super-elastic material for comparison. As known from FIG. 4, the yield load (yield stress) and the recovery load (recovery stress) of the core member 10 are smaller than those of the wire for comparison. Moreover, when the straight line for elastic range reaches the yield point, the straight line for the super elastic range extends from the yield point at a different angle. This indicates a wider elastic range. The core member 10 of this invention with this stress-strain characteristic is obtained by performing a heat treatment at a temperature of 450° to 550° C. for a time of about 30 seconds to 2 minutes.

FIGS. 5(a) and 5(b) are diagrams showing the torque-transmitting capabilities of these super-elastic core members. A vinyl chloride tube, 6 mm in inner diameter, was bent in a U shape with a curvature of 30 mm and filled with water of 20° C. Each core member made of Ni—Ti alloy was put in the tube and one end was driven to rotate at 1.5 rpm. The relationship between the angle of turn at the driven end (horizontal axis) and that of the free end (vertical axis) was measured. The broken line in each graph shows the ideal torque-transmitting capability in which the angle of turn at the free end is always equal to the angle of turn at the driven end.

FIG. 5(a) shows the test results of the above heat-treated wire (the core member of the invention). FIG. 5(b) shows the test results of a wire not heat-treated. There is about 45 degrees of difference at maximum between the angles of the two ends of the untreated wire. On the other hand, the angles of the two ends of the treated wire are almost same to the ideal line. This means that the turn applied to the proximal portion of the core member (the treated wire) is transmitted smoothly to the distal end without occurrence on bounces.

FIGS. 6(a) and 6(b) are line graphs which show the rigidities of super-elastic core members made of Ni—Ti alloy. Two samples of Ni—Ti alloy wire with an outer diameter of 0.5 mm were prepared: one heat-treated (B) and the other one not heat-treated (A). In a thermostatic chamber, a load was applied to the middle point of the 25 mm span of each sample and the load was measured when the middle point was pressed down 2 mm (speed of 5 mm/min). As known from FIG. 6(a), these two samples have nearly equal rigidities at 20° C. as known from FIG. 6(a), the heat-treated sample (B) has a higher rigidity than the untreated sample (A) at 40° C., which is equal to or greater than 1.5 times its rigidity 20° C. This means that the rigidity of the part of the super-elastic core member treated the above heating inserted into blood vessels considerably increases because of the body temperature, resulting in a higher torque-transmitting capability and pushability.

The X-ray opaque metal coil 20 is attached to the distal section 14 of the core member 10 in tight contact with the surface of the core member. The X-ray opaque metal coil 20 is made of gold. The length of the metal coil 20 in the direction of the axis is 20 mm. The diameter of the wire of the metal coil 20 is about 0.1 mm. The wire is wound on the core member 10 in tight contact with the surface of the core member and closely substantially without spaces between turns. The outer diameter of the metal coil 20 wound on the core member 10 is about the same as that of the proximal section 12. The front and rear ends of the metal coil 20 are secured to the core member 10 by bonded parts 22. An adhesive is used for bonding.

The synthetic resin envelope 30 is formed so that it covers the core member 10 and the X-ray opaque metal coil 20 and provides a substantially smooth outside surface. The guide wire 1 covered with the envelope 30 has an approximately uniform outer diameter. The envelope 30 is formed of a synthetic resin because of a synthetic resin being easy to form and the surface of the synthetic resin envelope being easy to treat as described below. The envelope 30 is flexible enough not to prevent bending of the core member, and the outside surface is substantially smooth. The envelope 30 covers the outside surface of the metal coil 20 and restricts the movement of the metal coil 20. Since the metal coil 20 is secured to the core member only at its ends, the metal coil 20 can move to a certain extent. For the synthetic resin for the envelope 30, a thermoplastic resin is preferable because of its being easy to form. thermoplastic polyurethane is used for this embodiment.

The synthetic resin of the envelope 30 contains 45 wt % of tungsten as the X-ray opaque substance. By covering the core member 10 with the envelope 30 containing an X-ray opaque substance, the X-ray visibility of the entire guide wire is improved.

The hydrophilic lubricative layer 40 covers the outside surface of the synthetic resin envelope 30, and becomes lubricative when it comes into contact with blood or an aqueous liquid, making easier the forward movement of the guide wire in blood vessels and increasing the slipperiness against the inside surface of the lumen of a catheter. For the purpose of passing through stenosed parts in blood vessels, the hydrophilic lubricative layer 40 may be formed only on the distal section or only on the distal and intermediates sections. The hydrophilic lubricative layer 40 may not be formed the rear end portion of the guide wire. When the guide wire has a length of about 1800 mm, the hydrophilic lubricative layer may be formed about 500 to 1500 mm from the distal end toward the proximal end, preferably 500 to 1000 mm.

For the hydrophilic lubricative substance for forming the lubricative layer 40, polyalkylene glycol such as poly(vinyl alcohol) and polyethylene glycol, and maleic anhydride derivatives such as maleic anhydride-ethyl ester copolymer can be enumerated for example.

The outside surface of the synthetic resin envelope 30 may also be coated with an anticoagulant such as heparin and urokinase or an anti-thrombogenic material such as silicone rubber, block copolymer of urethane and silicone, or hydroxyethylmethacrylatestyrene copolymer.

Figure 2:
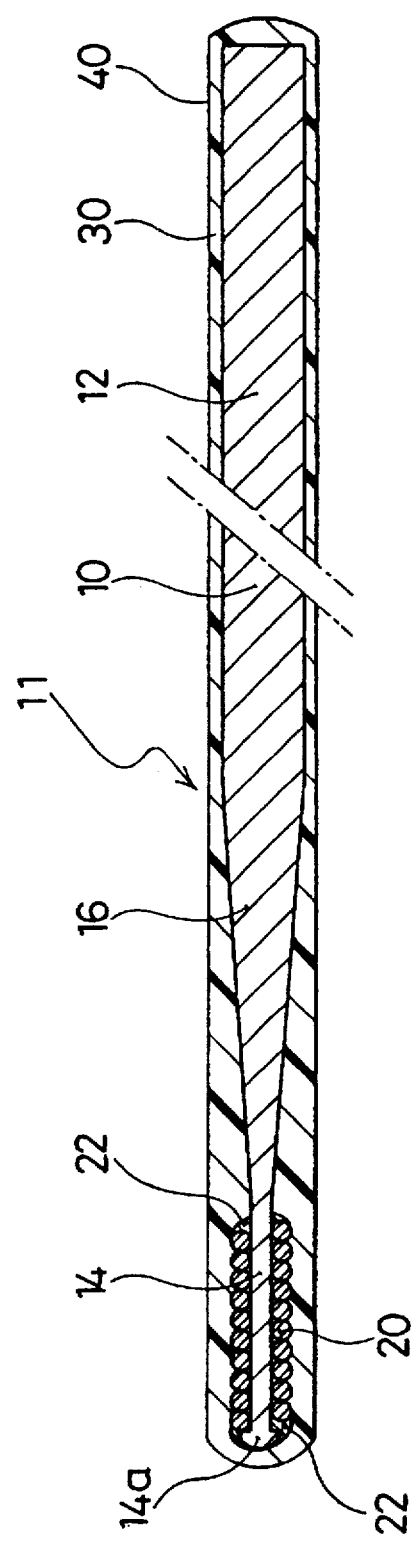
FIG. 2 is a sectional view of a second embodiment of a guide wire of the present invention.

Next, the guide wire shown in FIG. 2 is described.

FIG. 2 is a sectional view of the second embodiment of the guide wire of the present invention. The same structure as that in FIG. 1 is represented by the same reference numbers.

The guide wire 11 shown in FIG. 2 comprises a super-elastic core member 10 which consists of a proximal section 12, a distal section 14 smaller in diameter than the proximal section 12 and a intermediate section 16 between the proximal section 12 and the distal section 14, an X-ray opaque metal coil 20 attached to the distal section 14 of the core member 10 in tight contact with the distal section, a synthetic resin envelope 30 which covers the core member 10 and the X-ray opaque metal coil 20 to form a substantially smooth outside surface, and a hydrophilic lubricative layer 40 which covers the outside surface of the synthetic resin envelope 30. Further, an enlargement 14a is formed at the tip of the distal section 14.

The guide wire 1 of this embodiment has an overall length of 180 cm and an outer diameter of about 0.35 mm. The overall length of the guide wire 1 may be within the range of 80 to 500 cm. The outer diameter of the guide wire 1 is determined appropriately for the intended application, and the preferable outer diameter of the guide wire 1 for PTCA is equal to or smaller than 0.5 mm.

The super-elastic core member 10 consists of the proximal section 12, the intermediate section 16, and the distal section 14 and the enlargement at the tip of the distal section 14a.

The distal section 14 has an approximately uniform outer diameter and an approximately uniform flexibility. This portion is most flexible compared to the intermediate section 16 and the proximal section 12. The outer diameter of the distal section 14 is about 0.08 mm, and the length is about 20 mm. The enlargement 14a has a rounded head and is formed by melting the core member 10. The diameter of the enlargement 14a is greater than the outer diameter of the distal section 14 and the inner diameter of the metal coil 20, securing of the metal coil 20 to the core member 10 is made more reliable. The enlargement is formed by putting the metal coil 20 on the core member 10 and melting the tip of the core member 10 protruding through the metal coil 20.

The intermediate section 16 becomes gradually smaller in diameter toward the distal end. In this embodiment, the intermediate section 16 becomes gradually thinner at a uniform taper and can be referred to as the "tapered portion". The length of this intermediate section 16 is 300 mm. By forming this intermediate section 16, the flexibility (bendability) of the guide wire can be continuously increased toward the distal end without an abrupt change which can cause kinking.

The proximal section 12 extends from the intermediate section 16 to the proximal end of the guide wire 1. This proximal section has a substantially uniform outer diameter of about 0.3 mm and a length of about 1500 mm. The proximal section 12 is thicker than the distal section 14 so that it can transmit the torque and pushing force applied to the proximal portion to the distal section 14 with high fidelity.

The enlargement 14a, the distal section 14, the intermediate section 16 and the proximal section 12 of the core member 10 constitutes a single solid member made of the same material. By forming them in a single solid member, occurrence of breaking and kinking can be prevented. This core member 10 is made of a super elastic metal, Ni—Ti alloy. Being made of a super elastic metal, the core member 10 does not get into a habit of bending and has a high torque-transmitting capability even when it is in winding blood vessels.

The X-ray opaque metal coil 20 is attached to the distal section 14 of the core member 10 in tight contact with the surface of the core member. The X-ray opaque metal coil 20 is made of an alloy of 95% of platinum and 5% of iridium (Vickers Hardness: 90 to 180). This metal coil has an appropriate rigidity in addition to a high X-ray shadow producing capability. Because of this rigidity, the metal coil 20 can retain the new shape after plastic deformation and makes it possible to form the distal section of the core member into a desired shape. The length of the metal coil 20 in the direction of the axis is 20 mm. The diameter of the wire of the metal coil 20 is about 0.1 mm. The wire is wound on the core member 10 in tight contact with the surface of the core member and closely substantially without spaces between turns. The outer diameter of the metal coil 20 wound on the core member 10 is smaller than that of the proximal section 12. The front and rear ends of the metal coil 20 are secured to the core member 10 by bonded parts 22. An adhesive is used for bonding in this embodiment.

The synthetic resin envelope 30 is formed so that it covers the core member 10 and the X-ray opaque metal coil 20 and provides a substantially smooth outside surface. The guide wire 1 covered with the envelope 30 has an approximately uniform outer diameter. The envelope 30 is formed of a synthetic resin because of a synthetic resin being easy to form and the surface of the synthetic resin envelope being easy to treat as described below. The envelope 30 is flexible enough not to prevent bending of the core member 10, and the outside surface is substantially smooth. The envelope 30 covers the outside surface of the metal coil 20 and restricts the movement of the metal coil 20. Since the metal coil 20 is secured to the core member 10 only at its ends, the metal coil 20 can move to a certain extent. For the synthetic resin for the envelope 30, a thermoplastic resin is preferable because of its being easy to form. methacrylic acid-modified polyethylene is used for this embodiment.

The synthetic resin of the envelope 30 contains 45 wt % of tungsten as the X-ray opaque substance. By covering the core member 10 with the envelope 30 containing an X-ray opaque substance, the X-ray visibility of the entire guide wire is improved.

The hydrophilic lubricative layer 40 covers the outside surface of the synthetic resin envelope 30, and becomes lubricative when it comes into contact with blood or an aqueous liquid, making easier the forward movement of the guide wire in blood vessels and increasing the slipperiness against the inside surface of the lumen of a catheter. For the purpose of passing through stenosed parts in blood vessels, the hydrophilic lubricative layer 40 may be formed only on the distal section.

For the hydrophilic lubricative substance for forming the lubricative layer 40, poly(glycidyl methacrylate) (PGMA)-dimethyl acrylamide (DMAA), a block copolymer of hydrophilic compound and hydrophobic compound, is used.

Figure 3:
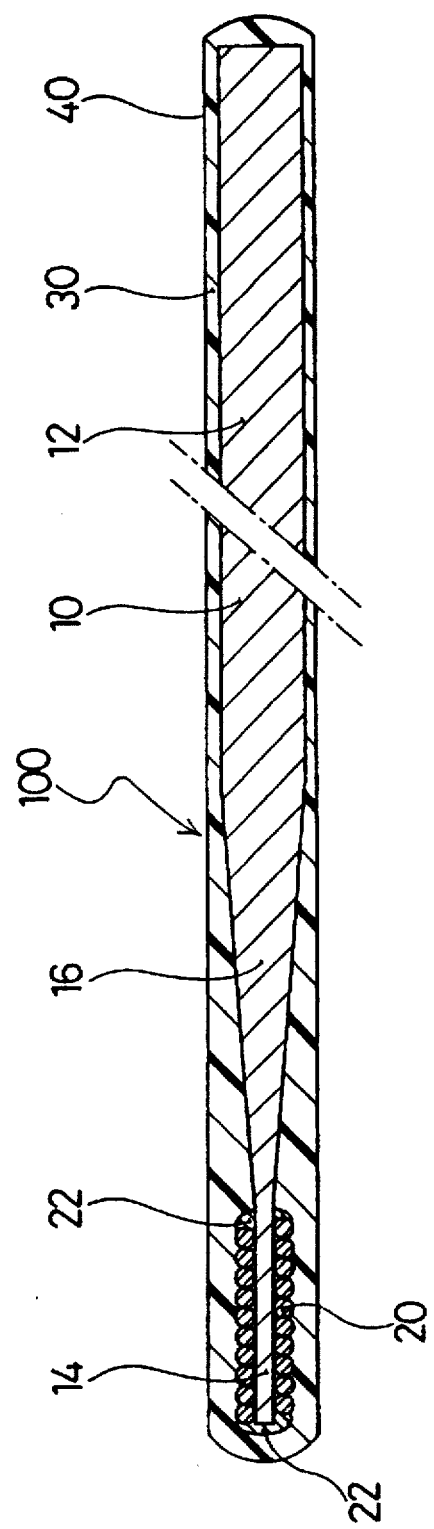
FIG. 3 is a sectional view of a third embodiment of a guide wire of the present invention.

Next, the guide wire shown in FIG. 3 is described.

FIG. 3 is a sectional view of the third embodiment of the guide wire of the present invention. The same structure as that in FIG. 1 is represented by the same reference numbers.

The guide wire 100 shown in FIG. 3 comprises a super-elastic core member 10 which consists of a proximal section 12, a distal section 14 smaller in diameter than the proximal section 12 and a intermediate section 16 between the proximal section 12 and the distal section 14, an X-ray opaque metal coil 20 attached to the distal section 14 of the core member 10 in tight contact with the distal section, a synthetic resin envelope 30 which covers the core member 10 and the X-ray opaque metal coil 20 to form a substantially smooth outside surface, and a hydrophilic lubricative layer 40 which covers the outside surface of the synthetic resin envelope 30. Further, the distal section 14 of the core member 10 has a capability (physical property) of retaining the shape it takes by reshaping from around room temperature to body temperature.

The guide wire 1 of this embodiment has an overall length of 180 cm and an outer diameter of about 0.35 mm.

The super-elastic core member 10 consists of the proximal section 12, the intermediate section 16, and the distal section 14.

The distal section 14 has an approximately uniform outer diameter and an approximately uniform flexibility, and is most flexible compared to the intermediate section 16 and the proximal section 12. The outer diameter of the distal section 14 is about 0.08 mm, and the length is about 20 mm.

A stress-strain curve of the core member used for the distal section is shown in FIG. 7. The diameter of the core member was about 0.335 mm. The core member was subjected to 5% tension test at 40° C. It is known from this diagram that about 1.8% of strain remains when applying 5% stress to the core member and then unloading. The distal section can be reshaped by hands.

The intermediate section 16 becomes gradually smaller in diameter toward the distal end. In this embodiment, the intermediate section 16 becomes gradually thinner at a uniform taper and can be referred to as the "tapered portion". The length of this intermediate section 16 is 300 mm. By forming this intermediate section 16, the flexibility (bendability) of the guide wire can be continuously increased toward the distal end without an abrupt change which can cause kinking.

The proximal section 12 extends from the intermediate section 16 to the proximal end of the guide wire 1. This proximal section has a substantially uniform outer diameter of about 0.3 mm and a length of about 1500 mm. The proximal section 12 is thicker than the distal section 14 so that it can transmit the torque and pushing force applied to the proximal portion to the distal section 14 with high fidelity.

The distal section 14, the intermediate section 16 and the proximal section 12 of the core member 10 constitutes a single solid member made of the same material. By forming them in a single solid member, occurrence of breaking and kinking can be prevented. This core member 10 is made of a supper elastic metal, Ni—Ti alloy. Being made of a super elastic metal, the core member 10 does not get into a habit of bending and has a high torque-transmitting capability even when it is in winding blood vessels.

The X-ray opaque metal coil 20 is attached to the distal section 14 of the core member 10 in tight contact with the surface of the core member. The X-ray opaque metal coil 20 is made of an alloy of 90% of platinum and 10% of iridium (Vickers Hardness: 120 to 240). This metal coil has an appropriate rigidity in addition to a high X-ray shadow producing capability. Because of this rigidity, the metal coil 20 can retain the new shape after plastic deformation and makes it possible to form the distal section of the core member into a desired shape. The length of the metal coil 20 in the direction of the axis is 20 mm. The diameter of the wire of the metal coil 20 is about 0.1 mm. The wire is wound on the core member 10 in tight contact with the surface of the core member and sparsely to form narrow spaces between turns as shown in FIG. 9. The coil 20 has a narrow spiral space. The outer diameter of the metal coil 20 wound on the core member 10 is a little smaller than that of the proximal section 12. The front and rear ends of the metal coil 20 are secured to the core member 10 by bonded parts 22. An adhesive is used for bonding in this embodiment.

The synthetic resin envelope 30 and the hydrophilic lubricative layer 40 are the same as those of the first embodiment.

Next, the function of the guide wire of this invention is described using the embodiment for PTCA.

First, a guiding catheter is advanced to the entrance of the coronary artery via an aorta. Next, a contrast medium is injected from the distal end of the guiding catheter into the coronary artery to make sure of the location of the stenosed part aimed at. Next, a dilation catheter with a balloon for widening a stenosed part near its distal end and the guide wire of the present invention are inserted. The guide wire of the present invention is passed through the guide wire lumen of the catheter in advance.

The distal section of the guide wire is reshaped beforehand into an appropriate shape matching the shape of branch in the blood vessel to make easier the insertion of the distal end of the guide wire into the blood vessel aimed at. Since a metal coil which undergoes plastic deformation is attached to the super-elastic core member which does not or not easily get into a habit of bending, the guide wire of the present invention can be reshaped repeatedly into any shape (shape in which about 5 mm of distal section bent at about 60 degrees, for example) because of the shape-retaining force of the metal coil exceeding the resilient force of the core member.

The dilation catheter with the guide wire being passed through the lumen is inserted into the guiding catheter. When the distal end of the dilation catheter reaches the distal end of the guiding catheter, the insertion of the dilation catheter is stopped, and the guide wire alone is advanced into the coronary artery, monitoring with a fluoroscope as necessary. Since this guide wire of the present invention is provided with the X-ray opaque metal coil at the distal section, the distal end of the guide wire can be easily located.

When insertion of the guide wire into the predetermined branch is difficult or when selection of another branch is desired, the guide wire can be pulled out and reshaped again. Since the core member has a super elasticity, it does not or not easily gets into a habit of bending. The reshape is retained by the metal coil. The guide wire can be reshaped repeatedly into any desired form. The metal coil is covered with the synthetic resin envelope and not secured to the core member except its ends. Therefore, the distal section of the guide wire is bent to reshape, the synthetic resin envelope hinders the movement of the coil. However, the spaces of the turns of the metal coil are widened at the outside of the curve and narrowed at the inside with the turns overlapping to some extent by stroking movement of fingers. Once the distal section is bent into a desired shape, the shape is retained by the plastic deformation of the metal coil and the restraint imposed by the synthetic resin envelope and not easily deformed by the insertion into a catheter.

When the guide wire reaches the stenosed part, it is pushed in being rotated slowly to pass through the stenosed part. Because of the high torque-transmitting capability of the super-elastic core member, the substantially smooth outside surface of the synthetic resin envelope, and the high lubricity of the hydrophilic lubricative layer over the outside surface of the synthetic resin envelope, the rotation of the proximal side is smoothly transmitted to the distal end, and the distal end rotates smoothly without bouncing. Therefore, passing of the guide wire through stenosed parts is made easier.

Then, the dilation catheter is advanced along the guide wire, the balloon is positioned at the stenosed part, and a pressured contrast medium is introduced into the balloon to widen the stenosed part. After the dilation is completed, the dilation catheter is pulled out.

The guide wire of the present invention can also be used for guiding various catheters such as contrast-medium injection catheters for brain or abdominal part and treatment catheters, though described above as for PTCA.

The guide wire of the present invention is thus reshapable, repeatedly and accurately in any desired form, has a high X-ray visibility, and can be easily passed through stenosed parts. A contrast medium is injected into blood vessels intermittently to identify the desired coronary artery with irradiation of X rays. Manipulation of the distal end of the guide wire is also performed keeping track of the position of the distal end with irradiation of X rays. Therefore, there is desired for the distal end of the wire than that of the contrast medium used for angiography.

Further, to advance the guide wire inserted from the femoral artery into the coronary artery via the aorta, the aortic arch and the entrance of the coronary artery, a sufficient flexibility needed to bend along the blood vessels and a high capability of transmitting the pushing force applied to the distal side to the distal end (pushability) are required.

What is claimed is:

1. A guide wire for a catheter comprising:
   a super-elastic core member having a proximal section, a distal section smaller in diameter than said proximal section and an intermediate section between said proximal section and said distal section, the distal section of said core member having an outer diameter that is substantially uniform or that becomes gradually smaller toward a distal end of the core member, said distal section having an outer peripheral surface;
   a shape deformable and deformed shape retaining X-ray opaque metal coil attached to said distal section of said core member, said metal coil being in tight contact with the outer peripheral surface of said distal section of said core member along the entire length of the metal coil, said metal coil having an outer surface;
   a synthetic resin envelope which covers said core member and said X-ray opaque metal coil to form a substantially smooth outside surface, the synthetic resin envelope contacting the outer surface of the metal coil, including filling up areas along the outer surface of the metal coil between adjacent turns of the metal coil, to restrict movement of the metal coil; and
   a hydrophilic lubricative layer which covers said outside surface of said synthetic resin envelope.

2. The guide wire of claim 1, wherein said super-elastic core member is made of Ni—Ti alloy.

3. The guide wire of claim 1, wherein said intermediate section is more flexible than said proximal section, and said distal section is more flexible tan said intermediate section.

4. The guide wire of claim 1, wherein said intermediate section becomes gradually smaller in outer diameter toward said distal end.

5. The guide wire of claim 1, wherein said intermediate section includes a first intermediate section which becomes smaller in diameter along a first taper and a second intermediate section which becomes smaller in diameter along a second taper that is greater than said first taper.

6. The guide wire of claim 1, wherein said synthetic resin envelope contains an X-ray opaque substance.

7. The guide wire of claim 1, wherein said wire coil includes oppositely located first and second ends, said first end of said coil being located closer to the distal end of the core member than the second end, the first end of said coil being secured to said super-elastic core member.

8. The guide wire of claim 1, wherein said wire coil includes oppositely located first and second ends, said first end of said coil being located closer to the distal end of the core member than the second end, the second end of said coil being secured to said super-elastic core member.

9. The guide wire of claim 1, wherein said wire coil includes oppositely located first and second ends, said first end of said coil being located closer to the distal end of the core member than the second end, wherein an intermediate portion of said coil located between said first and second ends is not secured to said super-elastic core member.

10. The guide wire of claim 1, wherein a front end and a rear end of said coil are secured to said super-elastic core member.

11. The guide wire of claim 1, wherein said hydrophilic lubricative layer is fixed to said outside surface of said synthetic resin envelope.

12. The guide wire of claim 1, wherein said hydrophilic lubricative layer covers said outside surface of said synthetic resin envelope except for a proximal portion of said guide wire.

13. The guide wire of claim 1, wherein said guide wire has an approximately uniform outer diameter from a distal end to a proximal end.

14. The guide wire of claim 1, wherein a length of said metal coil in the direction of an axis is within a range of 10 to 40 mm.

15. The guide wire of claim 1, wherein a material for said coil has a Vickers Hardness preferably within a range of 90 to 300.

16. The guide wire of claim 1, wherein said coil has a narrow spiral space.

17. The guide wire of claim 1, wherein said coil is made of a wire having oppositely located ends that are cut at an approximately right angle with the center axis of said wire.

18. The guide wire of claim 9, wherein said coil has a narrow spiral space.

19. The guide wire of claim 10, wherein said coil is made of a wire having oppositely located ends that are cut at an approximately right angle with the center axis of said wire.

20. The guide wire of claim 9, wherein said coil has oppositely located first and second ends that are secured to said super-elastic core member and said coil has a narrow spiral space, said first end of said coil being located closer to the distal end of the core member than the second end of the coil, said first and second ends of the coil being secured to said super-elastic core member, an intermediate portion of said coil located between said first and second ends being not secured to said super-elastic core member.

21. The guide wire of claim 18, wherein said coil is made of a wire having oppositely located ends that are cut at an approximately right angle with the center axis of said wire.

22. The guide wire of claim 1, wherein said coil is made of a material having a Vickers Hardness within the range of 90 to 300.

23. The guide wire of claim 1, wherein said coil is made of an alloy of platinum and iridium.

24. A guide wire for a catheter comprising:
   a super-elastic core member having a proximal section, a distal section smaller in diameter than said proximal section and an intermediate section between said proximal section and said distal section, said distal section having an outer peripheral surface;
   an X-ray opaque metal coil attached to said distal section of said core member, said metal coil being in tight contact with the outer peripheral surface of said distal section along the entire length of the metal coil, said metal coil attached to said distal section having characteristics which allow said metal coil to be repeatedly reshaped and to retain different shapes, said metal coil having an outer surface;

a synthetic resin envelope which covers said core member and said X-ray opaque metal coil to form a substantially smooth outside surface, the synthetic resin envelope contacting the outer surface of the metal coil, including filling up areas along the outer surface of the metal coil between adjacent turns of the metal coil, to restrict movement of the metal coil; and a hydrophilic lubricative layer which covers said outside surface of said synthetic resin envelope.

25. The guide wire of claim 24, wherein said metal coil possesses a Vickers Hardness of 90–300.

26. A guide wire for a catheter comprising:

a core member having a proximal section, a distal section smaller in diameter than said proximal section and an intermediate section between said proximal section and said distal section, the distal section of said core member having an outer diameter that is substantially uniform or that becomes gradually smaller toward a distal end of the core member, the distal section of the core member being made of a super-elastic material;

a shape deformable and deformed shape retaining X-ray opaque metal coil attached to said distal section of said core member, said metal coil being in tight contact with an outer surface of said distal section of said core member along the entire longitudinal extent of the metal coil, said metal coil having a front end and a rear end and possessing an outer surface; and a synthetic resin envelope which covers said core member and said x-ray opaque metal coil to form a substantially smooth outside surface, a front end of the synthetic resin envelope being positioned at the distal side from the front end of the metal coil and a rear end of the synthetic resin envelope being positioned at the proximal side from the rear end of the metal coil, the synthetic resin envelope contacting the outer surface of the metal coil, including filling up areas along the outer surface of the metal coil between adjacent turns of the metal coil, to restrict movement of the metal coil.

27. A guide wire for a catheter comprising:

a super-elastic core member having a proximal section, a distal section smaller in diameter than said proximal section and an intermediate section between said proximal section and said distal section, the distal section of said core member having an outer diameter that is substantially uniform or that becomes gradually smaller toward a distal end of the core member, said core member having a stress-strain characteristic obtained by performing heat treatment at a temperature of 450° to 550° C. for a time of about 30 seconds to 2 minutes;

a shape deformable and deformed shape retaining X-ray opaque metal coil attached to said distal section of said core member, said metal coil being in tight contact with an outer surface of said distal section of said core member along the entire longitudinal extent of the metal coil, said metal coil possessing an outer surface and being made of a material having a Vickers Hardness within the range of 90 to 300; and a synthetic resin envelope which covers said core member and said X-ray opaque metal coil to form a substantially smooth outside surface, the synthetic resin envelope contacting the outer surface of the metal coil, including filling up areas along the outer surface of the metal coil between adjacent turns of the metal coil, to restrict movement of the metal coil.

28. The guide wire of claim 27, wherein said coil is made of an alloy of platinum and iridium.

29. The guide wire of claim 27, wherein said coil is made of an alloy of platinum within the range of 90% to 95% and iridium within the range of 10% to 5%.

30. A guide wire for a catheter comprising:

a super-elastic core member having a proximal section, a distal section smaller in diameter than said proximal section and an intermediate section between said proximal section and said distal section, the distal section of said core member having an outer diameter that is substantially uniform or that becomes gradually smaller toward a distal end of the core member, the distal section of the core member having a physical property allowing the distal section of the core member to retain a shape upon being reshaped from around room temperature to body temperature;

a shape deformable and deformed shape retaining X-ray opaque metal coil attached to said distal section of said core member, said metal coil being in tight contact with an outer surface of said distal section of said core member along the entire longitudinal extent of the metal coil, said metal coil possessing an outer surface and being made of an alloy having a Vickers Hardness within the range of 120 to 240; and a synthetic resin envelope which covers said core member and said X-ray opaque metal coil to form a substantially smooth outside surface, the synthetic resin envelope contacting the outer surface of the metal coil, including filling up areas along the outer surface of the metal coil between adjacent turns of the metal coil, to restrict movement of the metal coil.

31. The guide wire of claim 30, wherein said coil is made of an alloy of platinum and iridium.

* * * * *

UNITED STATES PATENT AND TRADEMARK OFFICE
CERTIFICATE OF CORRECTION

PATENT NO. : 5,797,857
DATED : August 25, 1998
INVENTOR(S) : Hideshi OBITSU

It is certified that error appears in the above-identified patent and that said Letters Patent is hereby corrected as shown below:

In Column 4, line 48, delete "0-12" and insert -- 0.12 --.

In Column 5, line 37, delete "112" and insert -- ½ --.

Signed and Sealed this

Fifteenth Day of December, 1998

*Attest:*

BRUCE LEHMAN

*Attesting Officer*  Commissioner of Patents and Trademarks